United States Patent [19]

Kraatz et al.

[11] Patent Number: 4,592,772

[45] Date of Patent: Jun. 3, 1986

[54] (−)-ANTIPODE OF (E)-1-CYCLOHEXYL-4,4-DIMETHYL-3-HYDROXY-2-(1,2,4-TRIAZOL-1-YL)-PENT-1-ENE

[75] Inventors: Udo Kraatz, Leverkusen; Wolf Reiser, Wuppertal; Karl H. Büchel, Burscheid; Klaus Lürssen, Bergisch Gladbach, all of Fed. Rep. of Germany

[73] Assignee: Bayer Aktiengesellschaft, Leverkusen, Fed. Rep. of Germany

[21] Appl. No.: 571,019

[22] Filed: Jan. 16, 1984

[30] Foreign Application Priority Data

Jan. 22, 1983 [DE] Fed. Rep. of Germany ....... 3302122

[51] Int. Cl.⁴ .................. A01N 43/647; C07D 249/08
[52] U.S. Cl. ........................................... 71/76; 71/78; 71/92; 548/262
[58] Field of Search ...................... 548/262; 71/76, 78, 71/92

[56] References Cited

U.S. PATENT DOCUMENTS 4,435,203 3/1984 Funaki et al. ................ 548/262
4,486,218 12/1984 Reiser et al. ...................... 71/77

FOREIGN PATENT DOCUMENTS 2906061 1/1981 Fed. Rep. of Germany ...... 548/262

OTHER PUBLICATIONS

Karrer, Organic Chemistry (Second English Edition, N.Y., 1946), pp. 93–97.

*Primary Examiner*—Alton D. Rollins
*Attorney, Agent, or Firm*—Sprung, Horn, Kramer & Woods

[57] ABSTRACT

(−)-Antipode of (E)-1-cyclohexyl-4,4-dimethyl-3-hydroxy-2-(1,2,4-triazol-1-yl)-pent-1-ene of the formula

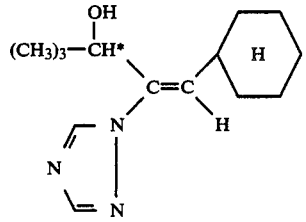

a plant growth regulant containing the same and a process for regulating the growth of plants are disclosed. Also disclosed is a method for making such antipode.

11 Claims, No Drawings

(−)-ANTIPODE OF (E)-1-CYCLOHEXYL-4,4-DIMETHYL-3-HYDROXY-2-(1,2,4-TRIAZOL-1-YL)-PENT-1-ENE

The present invention relates to the new (−)-antipode) of (E)-1-cyclohexyl-4,4-dimethyl-3-hydroxy-2-(1,2,4-triazol-1-yl)-pent-1-ene, a process for its preparation and its use for regulating plant growth.

(*) (-)-Antipode in this context is always to be understood as meaning the enantiomer which rotates the plane of vibration of linearly polarised light of the sodium D line to the left.

It is already known that the racemate of 1-cyclohexyl-4,4-dimethyl-3-hydroxy-2-(1,2,4-triazol-1-yl)-pent-1-ene has plant growth-regulating properties (compare DE-OS [German Published Specification] 2,906,061). The activity of this product is good, but the effect achieved is not always satisfactory when very low amounts are applied.

The (−)-antipode of (E)-1-cyclohexyl-4,4-dimethyl-3-hydroxy-2-(1 2,4-triazol-1-yl)-pent-1-ene of the formula

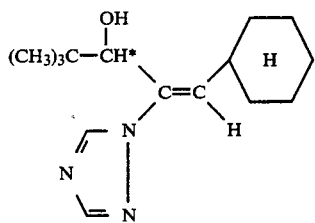
(I)

has now been found.

It has furthermore been found that the new (−)-antipode of (E)-1-cyclohexyl-4,4-dimethyl-3-hydroxy-2-(1,2,4-triazol-1-yl)-pent-1-ene of the formula (I) is obtained if, in a first stage, racemic (E)-1-cyclohexyl-4,4-dimethyl-3-hydroxy-2-(1,2,4-triazol-1-yl)-pent-1-ene of the formula

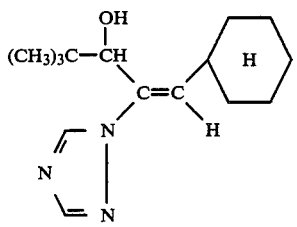
(Ia)

is reacted with an optically active acid halide of the formula

R—X—Hal         (II)

in which

R represents an optically active radical,

X represents —CO—, —SO$_2$— or —O—CH$_2$—CO— and

Hal represents halogen, in the presence of a diluent and, if appropriate, in the presence of bases, and the resulting diastereomeric esters of the formula

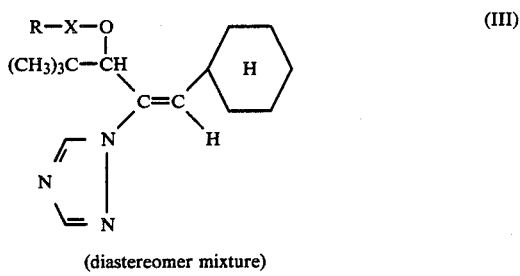
(III)

(diastereomer mixture)

in which

R and X have the abovementioned meaning, are then separated on the basis of their different physical properties, and, thereafter, in a second stage, the (−)-antipode of (E)-1-cyclohexyl-4,4-dimethyl-3-hydroxy-2-(1,2,4-triazol-1-yl)-pent-1-ene is liberated from the corresponding ester with the aid of bases in the presence of a diluent.

Finally, it has been found that the new (−)-antipode of (E)-1-cyclohexyl-4,4-dimethyl-3-hydroxy-2-(1,2,4-triazol-1-yl)-pent-1-ene of the formula (I) is distinguished by an outstanding plant growth-regulating activity.

Surprisingly, the new (−)-antipode of (E)-1-cyclohexyl-4,4-dimethyl-3-hydroxy-2-(1,2,4-triazol-1-yl)-pent-1-ene of the formula (I) has substantially better plant growth-regulating properties than the corresponding racemate, which is known as a highly effective plant growth regulator from the prior art. Moreover, it was not to be expected that the active compound according to the invention is distinguished by a very good plant growth-regulating activity, whilst the (+)-antipode of (E)-1-cyclohexyl-4,4-dimethyl-3-hydroxy-2-(1,2,4-triazol-1-yl)-pent-1-ene is largely inactive as a plant growth regulator.

Formula (I) provides a definition of the compound according to the invention. In this formula, the asymmetric carbon atom is labelled by (*).

If racemic (E)-1-cyclohexyl-4,4-dimethyl-3-hydroxy-2-(1,2,4-triazol-1-yl)-pent-1-ene is used as the starting substance (−)-menth-3-yloxy-acetyl chloride is used as the optically active acid halide, triethylamine and 4-dimethylaminopyridine (DMPA) are used as auxiliary bases for the esterification (1st stage) and a mixture of sodium hydroxide, water and methanol is used for hydrolysing the ester (2nd stage), the course of the reaction in the process according to the invention can be represented by the following equation:

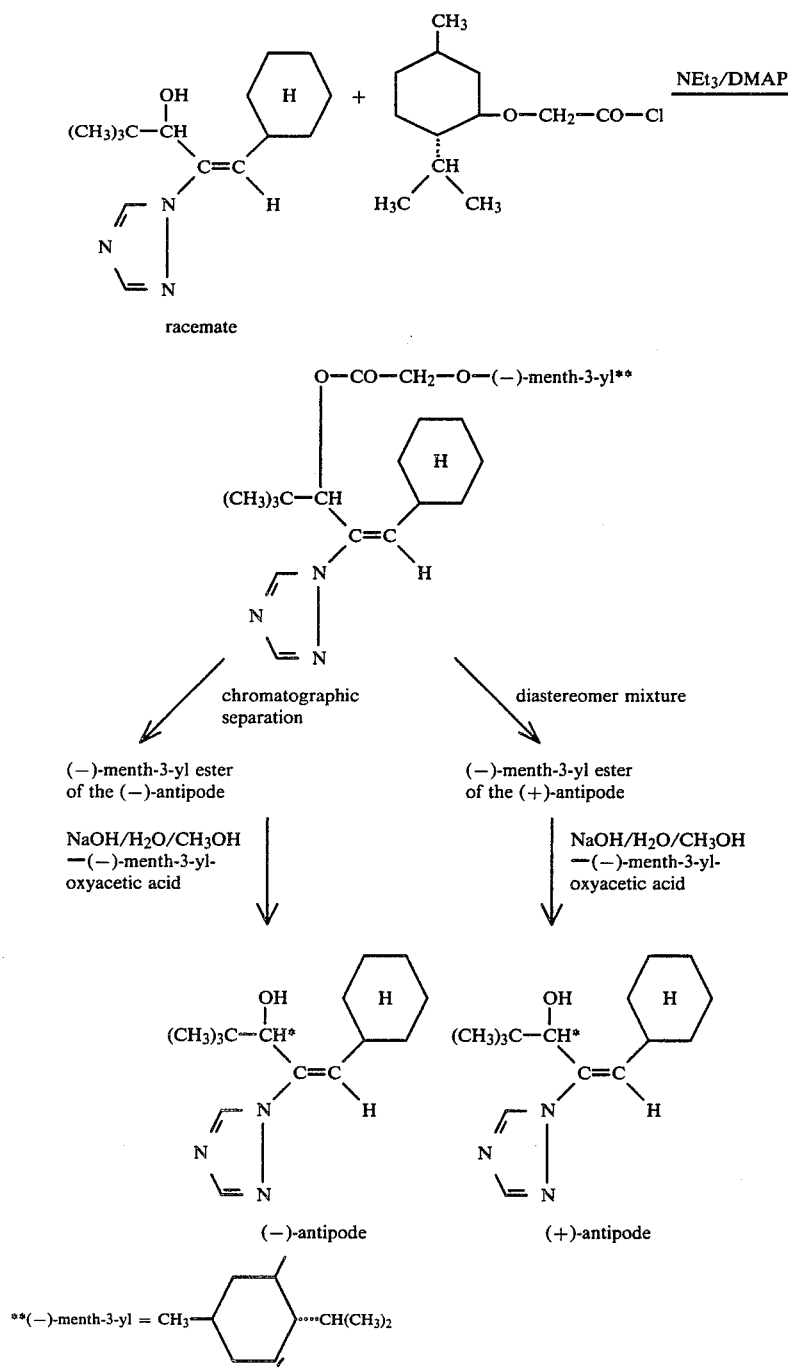

The racemate of (E)-1-cyclohexyl-4,4-dimethyl-3-hydroxy-2-(1,2,4-triazol-1-yl)-pent-1-ene of the formula (Ia) required as the starting substance for carrying out the process according to the invention is known (compare DE-OS [German Published Specification] 2,906,061).

Formula (II) provides a general definition of the optically active acid halides also required as starting substances in the process according to the invention. In this formula, R preferably represents (+)-3-bromocamphor-8-yl, (+)-camphor-10-yl or (−)-menth-3-yl. X represents the radicals —CO—, —SO$_2$— or —O—CH$_2$—CO—, and Hal preferably represents chlorine or bromine.

Examples of compounds of the formula (II) which may be mentioned are: (+)-3-bromo-camphor-8-sulphonyl chloride, (+)-camphor-10-sulphonyl chloride, (+)-3-bromocamphor-8-sulphonyl bromide, (+)-camphor-10-sulphonyl bromide, (−)-menth-3-yl-oxyacetyl chloride and (−)-menth-3-yl-oxyacetyl bromide.

The optically active acid halides are known, or they can be prepared in a simple manner by known methods.

Possible diluents for carrying out the 1st stage (esterification) of the process according to the invention are all the inert organic solvents. These include, preferably, hydrocarbons, such as benzine, benzene, toluene or xylene, halogenated hydrocarbons, such as methylene chloride, chloroform, carbon tetrachloride, chlorobenzene or dichlorobenzene, ethers, such as diethyl ether, tetrahydrofuran or dioxane, nitriles, such as acetonitrile or propionitrile, and esters, such as ethyl acetate.

The first stage of the process according to the invention is preferably carried out in the presence of bases. All the customary organic or inorganic bases can be used here. Bases which can preferably be used are alkali metal hydroxides or alkali metal carbonates, such as, for example, sodium hydroxide, sodium carbonate or sodium bicarbonate, and furthermore lower tertiary alkylamines, cycloalkylamines, arylalkylamines or arylamines, such as, for example, triethylamine, N,N-dimethylbenzylamine, pyridine, 1,4-diazabicyclo-[2,2,2]-octane or 1,5-diazabicyclo-[4,3,0]-non-5-ene. A mixture of triethylamine and the highly nucleophilic 4-dimethylaminopyridine is particularly preferably used.

The reaction temperatures can be varied within a substantial range in carrying out the 1st stage of the process according to the invention. In general, the reaction is carried out between $-20°$ C. and $+120°$ C., preferably between $0°$ C. and $60°$ C.

In carrying out the 1st stage of the process according to the invention, 1 to 1.5 mol of optically active acid halide of the formula (II) and 2 to 3 mol of base are preferably employed per mol of the racemic starting compounds of the formula (Ia). The diastereomer mixture is isolated by customary methods. In general, a procedure is followed in which, when the reaction has ended, water is added, the resulting mixture is extracted several times with an organic solvent of low water-miscibility and the combined organic phases are dried and concentrated under reduced pressure.

The diastereomeric esters of the formula (III) can be separated by methods suitable for such purposes, thus, for example, by fractional crystallisation or with the aid of chromatographic processes.

Column chromatography separation processes are particularly preferably used, such as, for example, high pressure filtration over a silica gel column using an elution mixture of hexane, carbon tetrachloride and propionitrile.

Inert organic solvents are likewise suitable diluents for the 2nd stage (ester hydrolysis) of the process according to the invention. Alcohols, such as, for example, methanol, ethanol or propanol, are particularly preferably used.

The active compound according to the invention is liberated in the second stage of the process according to the invention with the aid of bases. Strong aqueous inorganic bases, such as sodium hydroxide or potassium hydroxide in water, are preferably used for this.

The reaction temperatures can likewise be varied within a substantial range in carrying out the 2nd stage of the process according to the invention. In general, the reaction is carried out between $0°$ C. and $80°$ C., preferably between $10°$ C. and $60°$ C.

In carrying out the 2nd stage of the process according to the invention, 1 to 3 mol, preferably 1 to 2 mol, of base are in general employed per mol of the particular diastereomeric ester of the formula (III).

The active compound according to the invention is isolated by customary methods. In general, a procedure is followed in which water is added to the reaction mixture, the mixture is then extracted several times with an organic solvent of low water-miscibility, the combined organic phases are dried and concentrated by stripping off the solvent under reduced pressure and the residue which remains is, if necesary, freed from any impurities present by recrystallisation or by washing with an organic solvent.

In carrying out the second stage of the process according to the invention, in each case that diastereomeric ester of the formula (III) from which the $(-)$-antipode, according to the invention, of (E)-1-cyclohexyl-4,4-dimethyl-3-hydroxy-2-(1,2,4-triazol-1-yl)-pent-1-ene is liberated by treatment with base is employed.

The $(+)$-antipode of (E)-1-cyclohexyl-3-hydroxy-2-(1,2,4-triazol-1-yl)-pent-1-ene can also be prepared by the process according to the invention. In this case, the procedure is such that, after the diastereomeric esters have been separated, in each case that compound of the formula (III) which contains the $(+)$-antipode is treated with base in the presence of a diluent. The reaction conditions correspond to those suitable for carrying out the second stage in the case of the process according to the invention.

The active compound according to the invention engages in the metabolism of the plants and can therefore be employed as a growth regulator.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sports grounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a desired extent (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compound according to the invention can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compound with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example, crushed and fractionated natural rocks such as calcite, marble, pumice, sepiolite and dolomite, as well as synthetic granules of inorganic or organic meals, and granules of organic material such as sawdust, coconut shells, maize cobs and tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl-sulphates, arylsulphonates as well as albumin hydrolysation products. As dispersing agents there are suitable: for example, lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention an be present in the formulations as a mixture with other known active compounds, such as fungicides, insecticides, acaricides and herbicides, and also as mixtures with fertilisers and other growth regulators.

The active compound can be used as such, in the form of its formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomising, scattering, dusting, foaming, coating and the like. Furthermore, it is possible to apply the active compound in accordance with the ultra-low volume process or to inject the active compound preparation or the active compound itself into the soil. It is also possible to treat the seeds of plants.

The amounts applied can be varied within a substantial range. In general, 0.01 to 50 kg, preferably 0.05 to 10 kg, of the active compound are employed per hectare of soil surface.

As regards the time of application, the rule is that the growth regulators are applied within a preferred period of time, the exact definition of which depends on the climatic and vegetative circumstances.

The preparation and use of the active compounds according to the invention are illustrated by the following examples.

PREPARATION EXAMPLES

Example 1

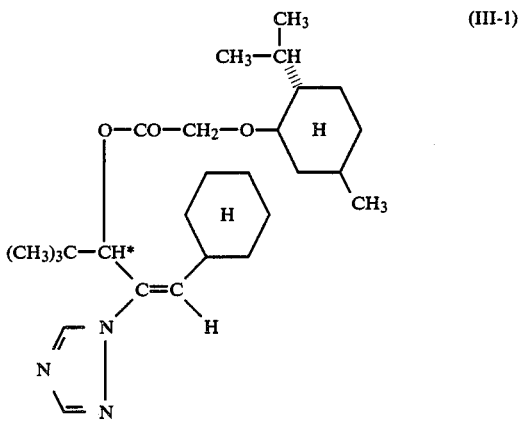
(III-1)

1st stage 11.7 g (0.0503 mol) of (−)-menth-3-yloxyacetyl chloride are added dropwise to 12.0 g (0.0456 mol) of racemic (E)-1-cyclohexyl-4,4-dimethyl-3-hydroxy-2-(1,2,4-triazol-1-yl)-pent-1-ene, 6.0 g (0.06 mol) of triethylamine and 7.32 g (0.06 mol) of 4-dimethylaminopyridine in 250 ml of absolute tetrahydrofuran, while stirring and cooling with ice, and, when the addition has ended, the mixture is stirred for a further 20 hours at 20° C. to 25° C. For working up, the reaction mixture is poured into 500 ml of water and extracted several times with methylene chloride, the combined organic extracts are dried over sodium sulphate and the solvent is removed in vacuo.

18.3 g (87.2% of theory) of (E)-1-cyclohexyl-4,4-dimethyl-3-(−)-(menth-3-yloxyacetyloxy)-2-(1,2,4-triazol-1-yl)-pent-1-ene diastereomer mixture are obtained as a highly viscous oil.

Separation into the individual diastereomeric components is carried out by means of HPLC) on a silica gel column (Merck 5–20μ particle size) using the eluant mixture hexane, carbon tetrachloride and propionitrile (7:2:1).

*)×High performance liquid chromatography 4.5 g (42.9% of theory) of the (−)-menth-3-yloxyacetate of the (+)-enantiomer of (E)-1-cyclohexyl-4,4-dimethyl-3-hydroxy-2-(1,2,4-triazol-1-yl)-pent-1-ene of refractive index $n_D^{20}$:1.4922 are eluted as the 1st fraction. 4.7 g (44.9% of theory) of the (−)-menth-3-xloxyacetate of the (−)-enantiomer of (E)-1-cyclohexyl-4,4-dimethyl-3-hydroxy-2-(1,2,4-triazol-1-yl)-pent-1-ene of refractive index $n_D^{20}$:1.4925 are eluted as the 2nd fraction.

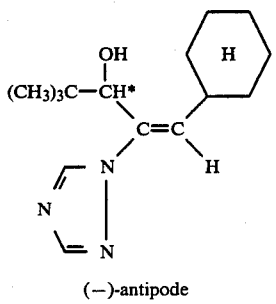

(−)-antipode

2nd stage

A solution of 0.6 g (0.015 mol) of sodium hydroxide in 5 ml of water is added to 4.65 g (0.0102 mol) of the 2nd ester fraction in 40 ml of methanol and the mixture is stirred at 20° C. to 25° C. for 3 hours. For working up, the mixture is diluted with 150 ml of water and extracted with three 120 ml portions of methylene chloride, the combined organic extracts are washed with water and dried over magnesium sulphate and the solvent is removed in vacuo. The solid residue is washed with cyclohexane and filtered off with suction.

1.9 g (70.9% of theory) of the (−)-antipode of (E)-1-cyclohexyl-4,4-dimethyl-3-hydroxy-2-(1,2,4-triazol-1-yl)-pent-1-ene of melting point 145° to 148° C. are obtained.

The product has an optical purity of 61%. $[\alpha]_D^{20} = -48.6°$ (c=87.5 mg/10 ml CHCl$_3$).

COMPARISON EXAMPLE I

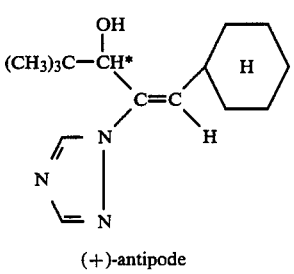

(+)-antipode

A solution of 0.6 g (0.015 mol) of sodium hydroxide in 5 ml of water is added to 4.49 g (0.00978 mol) of that diastereomer which has been obtained from the first fraction of the elution described in Example 1, first stage, in 40 ml of methanol and the mixture is stirred at 20° C. to 25° C. for 3 hours. For working up, the mixture is diluted with 150 ml of water and extracted with three 120 ml portions of methylene chloride, the combined organic extracts are washed with water and dried over magnesium sulphate and the solvent is removed in vacuo. The solid residue is washed with cyclohexane and filtered off with suction.

1.62 g (62.8% of theory) of the (+)-antipode of (E)-1-cyclohexyl-4,4-dimethyl-3-hydroxy-2-(1,2,4-triazol-1-yl)-pent-1-ene of melting point 159°–161° C. are obtained . The product has an optical purity of 98%. $[\alpha]_D^{20} = +77.3°$ (c=81.5 mg/10 ml CHCl$_3$).

COMPARISON EXAMPLE II

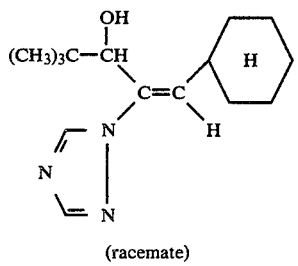

(racemate)

26 g (0.1 mol) of (E)-1-cyclohexyl-4,4-dimethy-2-(1,2,4-triazol-1-yl)-pent-1-en-3-one are taken up in 200 ml of methanol, and 4.5 g of sodium borohydride are added in portions, while stirring and cooling. When the reaction has ended, the reaction mixture is brought to pH 6 and concentrated. The residue is taken up 200 ml of methylene chloride, the mixture is washed with saturated sodium bicarbonate solution, dried over sodium sulphate and filtered and the filtrate is concentrated. The residue is recrystallised from petroleum ether. 14.5 g (55% of theory) of racemic (E)-1-cyclohexyl-4,4-dimethyl-3-hydroxy-2-(1,2,4-triazol-1-yl)-pent-1-ene of melting point 131° C. are obtained.

Preparation of the starting substance:

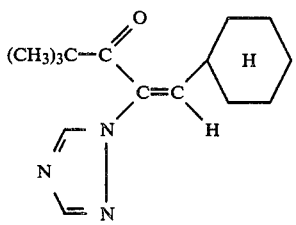

83.5 g (0.5 mol) of pinacolyl-1,2,4-triazole, 60 g (0.54 mol) of cyclohexanealdehyde, 4.2 g (0.05 mol) of piperidine and 6 g (0.1 mol) of glacial acetic acid in 300 ml of toluene are heated under reflux, using a water separator, until no further water passes over. After the reaction solution has been cooled, it is washed with saturated sodium chloride solution, the organic phase is dried over sodium sulphate and filtered and the filtrate is concentrated. The residue is taken up in 500 ml of acetone and a filtered solution of 90 g (0.25 mol) of naphthalene-1,5-disulphonic acid in 500 ml of acetone is added, while stirring.

The precipitate which initially separates out is filtered off with suction, the filtrate is concentrated further and the resulting colourless crystalline residue is taken up in 500 ml of methylene chloride. Thereafter, half-concentrated aqueous sodium bicarbonate solution is added until the mixture has an alkaline reaction. The organic phase is separated off, dried and filtered and the filtrate is concentrated. The oily residue is taken up in petroleum ether and the mixture is left to crystallise. 64 g (49% of theory) of (E)-1-cyclohexyl-4,4-dimethyl-2-(1,2,4-triazol-1-yl)-pent-1-en-3-one of melting point 98° C. are obtained.

EXAMPLE A

Inhibition of growth of barley

Solvent: 30 parts by weight of dimethylformamide

Emulsifier: 1 part by weight bf polyoxyethylene sorbitan monolaurate

To produce a suitable preparation of active compound, 1 part by weight of active compound is mixed with the stated amounts of solvent and emulsifier and the mixture is made up to the desired concentration with water.

Barley plants are grown in a greenhouse to the 2-leaf stage. In this stage, the plants are sprayed with the preparations of active compound until dripping wet. After 3 weeks, the additional growth of all the plants is measured and the inhibition of growth in per cent of the additional growth of the control plants is calculated. 100% inhibition of growth means that growth has stopped and 0% denotes a growth corresponding to that of the control plants.

The active compounds, active compound concentrations and test results can be seen from the following table.

TABLE A

| Inhibition of growth of barley | | |
|---|---|---|
| Active compound | Concentration in % | Inhibition in % |
| ![structure] OH (CH$_3$)$_3$C—CH, C=C, N, N=N (H, cyclohexyl, H) racemic (known) | 0.05 | 28 |
| ![structure] *OH (CH$_3$)$_3$C—CH, C=C, N, N=N (H, cyclohexyl, H) (−)-antipode (according to the invention) | 0.05 | 38 |

TABLE A-continued

| | Inhibition of growth of barley | |
|---|---|---|
| Active compound | Concentration in % | Inhibition in % |
| 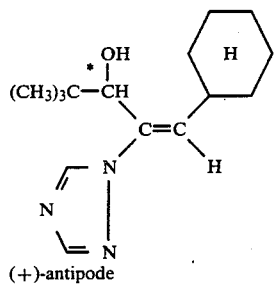<br>(+)-antipode | 0.05 | 5 |

EXAMPLE B

Inhibition of growth of soya bean

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Soya bean plants are grown in a greenhouse until the first secondary leaf has unfolded completely. In this stage, the plants are sprayed with the preparation of active compound until dripping wet. After 3 weeks, the additional growth of all the plants is measured and the inhibition of growth in per cent of the additional growth of the control plants is calculated. 100% inhibition of growth means that growth has stopped and 0% denotes a growth corresponding to that of the control plants.

The active compounds, active compound concentrations and test results can be seen from the following table.

TABLE B

| | Inhibition of growth of soya bean | |
|---|---|---|
| Active compound | Concentration in % | Inhibition in % |
| 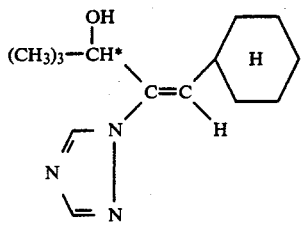<br>racemic (known) | 0.025 | 64 |
| 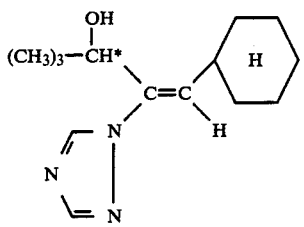<br>(−)-antipode (according to the invention) | 0.025 | 77 |

TABLE B-continued

| | Inhibition of growth of soya bean | |
|---|---|---|
| Active compound | Concentration in % | Inhibition in % |
| 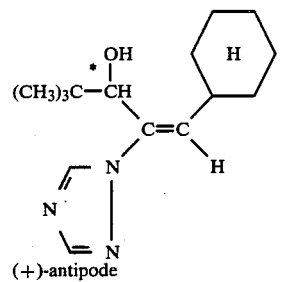<br>(+)-antipode | 0.025 | 0 |

What is claimed is:

1. A substantially pure (−)-antipode of (E)-1-cyclohexyl-4,4-dimethyl-3-hydroxy-2-(1,2,4-triazol-1-yl)-pent-1-ene of the formula

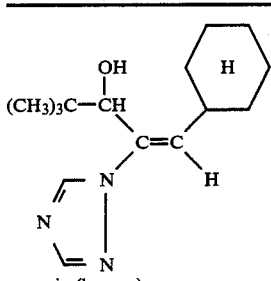

2. A plant growth regulating agent comprising an effective amount of (−)-antipode of (E)-1-cyclohexyl-4,4-dimethyl-3-hydroxy-2-(1,2,4-triazol-1-yl)-pent-1-ene of the formula

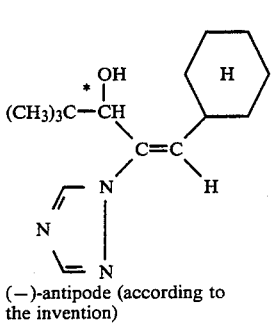

substantially free of the (+) antipode and a diluent.

3. A composition according to claim 2, wherein said antipode is present in said composition in an amount between 0.1 and 95% by weight.

4. A composition according to claim 3, wherein said diluent is a solid.

5. A composition according to claim 3, wherein said diluent is a liquid.

6. A composition according to claim 5, wherein said diluent is a solvent.

7. A composition according to claim 6, wherein said diluent is an aromatic hydrocarbon, chlorinated aromatic hydrocarbon, chlorinated aliphatic hydrocarbon, aliphatic hydrocarbon, alcohol, ether, ester, ketone, dimethylformamide or dimethylsulphoxide.

8. A process for regulating the growth of a plant which comprises applying to the plant or its habitat a plant growth regulatingly effective amount of the antipode of claim 1.

9. A process according to claim 8, wherein said antipode is applied to barley or its habitat.

10. A process according to claim 8, wherein said antipode is applied to soya bean or its habitat.

11. A composition according to claim 2, wherein said antipode is present in said composition in an amount of between 0.5 and 90% by weight.

* * * * *

UNITED STATES PATENT AND TRADEMARK OFFICE
CERTIFICATE OF CORRECTION

PATENT NO. : 4,592,772

DATED : June 3, 1986

INVENTOR(S) : Udo Kraatz, et al.

It is certified that error appears in the above-identified patent and that said Letters Patent is hereby corrected as shown below:

| | |
|---|---|
| Abstract, line 3; Col. 14, lines 23 and 38 | Delete beginning of formula and substitute: $-(CH_3)_3C-$ |
| Col. 1, line 9 | After "antipode" delete ")" and substitute --(*)-- |
| Col. 9, line 4 | End of line delete "an" and substitute --can-- |
| Col. 10, line 6 | After "HPLC" delete ")" and substitute --(*)-- |
| Col. 10, line 10 | After "*)" delete "x" and substitute -- = -- |
| Col. 10, line 15 | End of line delete "xlox-" and substitute --ylox- -- |
| Col. 12, line 16 | Delete "bf" and substitute --of-- |
| Col. 14, line 18 | After "1" insert -- - -- |
| Col. 14, line 45 | After "(+)" insert -- - -- |

Signed and Sealed this

Twenty-first Day of October, 1986

[SEAL]

Attest:

DONALD J. QUIGG

Attesting Officer

Commissioner of Patents and Trademarks